(12) United States Patent
Thomas et al.

(10) Patent No.: US 6,799,074 B1
(45) Date of Patent: Sep. 28, 2004

(54) MICROPROBE SYSTEM FOR STEREOTACTIC NEUROTHERAPY

(75) Inventors: Uwe Thomas, Marburg (DE); Dirk Hohl, Marburg (DE); Wilfried Gerber, Mocke (DE)

(73) Assignee: Uwe Thomas Recording, Giessen (DE)

( * ) Notice: Subject to any disclaimer, the term of this patent is extended or adjusted under 35 U.S.C. 154(b) by 285 days.

(21) Appl. No.: 09/639,156

(22) Filed: Aug. 16, 2000

(30) Foreign Application Priority Data

Aug. 18, 1999 (DE) .......................................... 199 38 549

(51) Int. Cl.[7] ................................................ A61N 1/18
(52) U.S. Cl. ...................................... 607/116; 606/130
(58) Field of Search .............................. 600/372, 373, 600/378, 383, 393, 544, 414, 417, 427, 429; 607/2, 45, 116; 606/129, 130; 604/174, 175

(56) References Cited

U.S. PATENT DOCUMENTS 5,399,256 A * 3/1995 Bohs et al. ................. 204/409
5,928,144 A * 7/1999 Real ........................... 600/378
6,109,270 A * 8/2000 Mah et al. .................. 128/920

* cited by examiner

Primary Examiner—Frances P. Oropeza
(74) Attorney, Agent, or Firm—Klaus J. Bach

(57) ABSTRACT

In a microprobe system for medical applications particularly for use in neurophysiology and neurosurgery a target determining arrangement is provided which can be mounted on a patients head by means of an adjustable mounting device. An adapter is removably attached to the mounting device and carries a manipulator with a removable probe unit that can be moved by a drive unit which is electrically controllable according to spatial coordinates (x,y,z—respectively, R,φ). The probe unit includes a guide tube for receiving an exchangeable microfiber electrode, which includes sensor areas at its pointed tip for the recording of brain activity signals. The signals can be stored with a PC-interface in a data acquisition unit, which is in communication with an output unit. The manipulator includes a microfiber electrode control unit, for example, an XYZ-slide with locking means as well as a base body for the attachment of the probe unit to the mounting device in a predetermined orientation.

18 Claims, 4 Drawing Sheets

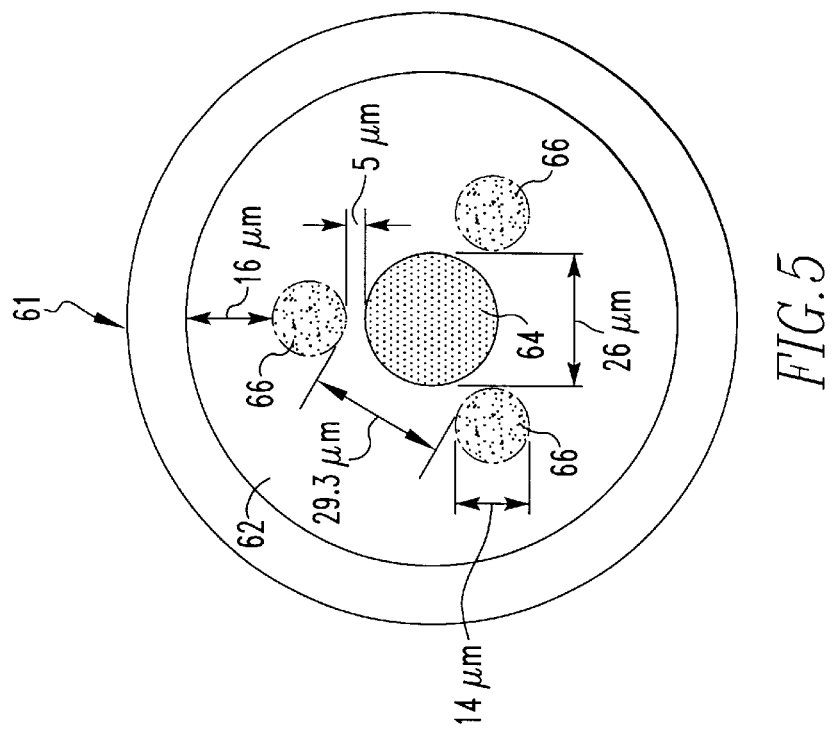
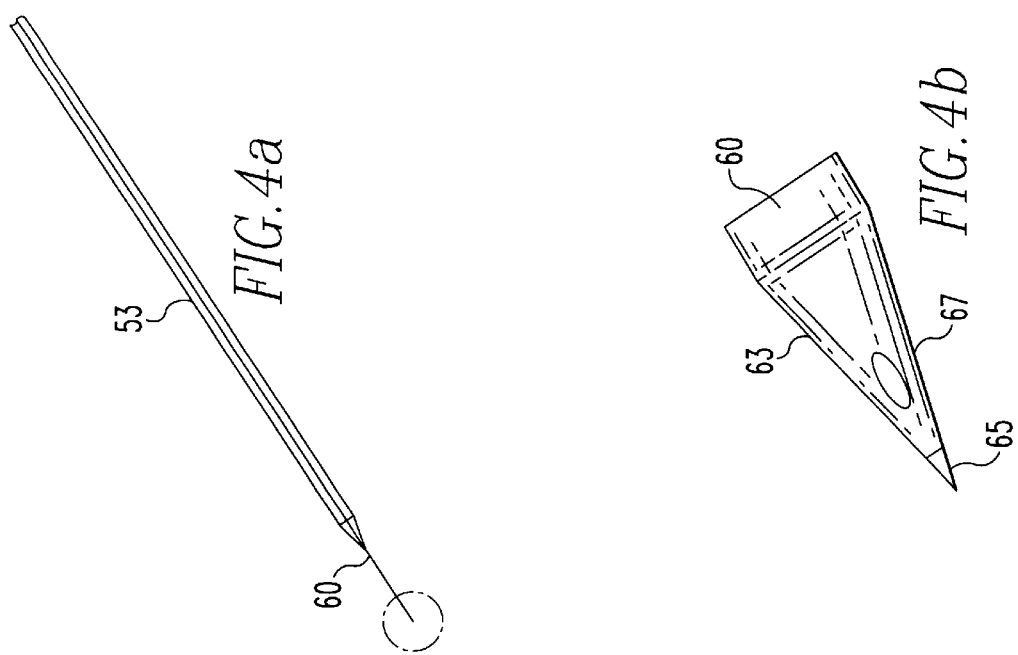

MICROPROBE SYSTEM FOR STEREOTACTIC NEUROTHERAPY

BACKGROUND OF THE INVENTION

The invention relates to a microprobe system particularly a microprobe system for medical applications especially for stereotactic neurotherapy.

In the medical field as well as in biological research, microprobes are used which are inserted into a tissue where a body structure is to be specifically influenced or scanned. A specific example is the treatment of essential tremor or—in connection with Parkinson's disease—of therapy-refracted tremors. To this end, a microelectrode is introduced in the ventral intermediate core (VIM) of the thalamus of a patient in an accurately controlled manner. This microelectrode is then connected to an electrical stimulator, which is implanted subcutaneously below the clavicle. Such a "brain pacemaker" can effectively stop the involuntary action tremor so that the quality of life of the patient is drastically improved.

For other diseases such as Akinese or drug-induced excess movements other targets will be used, i.e. the nucleus subthalamicus or the globus pallidus. Furthermore, brain areas, which are responsible for some disease symptoms, are being coagulated (destroyed) recently with the aid of microelectrodes. This procedure is different for different target areas. It is either pallidotomy (target area globus pallidus) or thalamotomy (target area thalamus).

The location is usually determined with electrophysiological depth recordings of neuronal discharge patterns along a given stereotactic path. The correct determination of a naturally very small target area in the brain is always crucial because a displaced pacemaker electrode would damage, and stimulate, neighboring brain areas, i.e.—fiber sections such as the visual or the pyramid lines.

Conventional recording systems have manual micrometer propulsions, which only permit a relatively inaccurate positioning which is afflicted with errors. Usually, the microelectrode position is only read from a micrometer screw and then manually recorded in an operation protocol. The values may include reading mistakes and inaccuracies. The microelectrode position is not recorded simultaneously with the digitally recorded sensor values. Furthermore, during the electrode forward feeding, the signal recording is susceptible to errors. Due to their dimensions, the recording electrodes are mostly not selective enough to scan individual cells. Therefore, the probability of the signal recording being correct is relatively low. All these circumstances result in a prolonged operations and uncertain success.

Another essential disadvantage of the conventional techniques is the fact that the macro therapy electrode (brain pacemaker) may shift from its position after it has been accurately positioned and part of the stereotactic system (guide tube) is removed. In order to correct any error caused thereby the therapy electrode has to be re-positioned which is quite difficult. A new manual search of the target point determined in advance is necessary with the aid of the described stereotactic measures without the stereotactic aids, which is time consuming and unnecessarily prolongs the operation.

It is an important object of this invention to overcome these and other disadvantages of the state of the art with the most economic means and to create an improved microprobe system that operates with high precision of positioning at a considerably reduced operating time and, at the same time, provides for a documentation permitting a reconstruction of the procedure in order to obtain further information.

SUMMARY OF THE INVENTION

In a microprobe system for medical applications particularly for use in neurophysiology and neurosurgery a target determining arrangement is provided which can be mounted on a patients head by means of an adjustable mounting device. An adapter is removably attached to the mounting device and carries a manipulator with a removable probe unit that can be moved by a drive unit which is electrically controllable according to spatial coordinates (x,y,z—respectively, R,ϕ). The probe unit includes a guide tube for receiving an exchangeable microfiber electrode, which includes sensor areas at its pointed tip for the recording of brain activity signals. They can be stored with a PC-interface in a data acquisition unit, which is in communication with an output unit. The manipulator includes a microfiber electrode control unit, for example, an XYZ-slide with locking means as well as a base body for the attachment of the probe unit to the mounting device in a predetermined orientation.

This new system is distinguished by an exactly controllable, propulsion arrangement, whereby manual uncertainties are avoided. The microfiber electrode delivers neuronal signals during its movement which signals are processed and continuously recorded in the data acqustion unit together with the extremely accurate instant data concerning the microelectrode position. This permits an exceptionally precise error-free guidance of the microprobe into the target area. In contrast to the necessity of prior art arrangements to record the signal and micro-stimulate the tissue in separate processes, one after the other, the system according to the invention integrates these steps with the effect that the operation time is greatly shortened. Since the exact position of the microfiber electrode is digitally recorded and evaluated at any time, all data for the placement of the actual macro therapy electrode are fully available and controllable at any time, either by way of monitor or loudspeaker presentation or by a print-out of a protocol.

Preferably, the manipulator includes a carrier unit for the alignment and guiding of the microfiber electrode and/or the macro therapy electrode along the preferred direction, which preferably includes a guide tube in which the microelectrode and the macro therapy electrode can be inserted alternately. The carrier unit provides always for an identical alignment of the electrodes, which have to be inserted successively so that a certain position established with the microelectrode can be accurately assumed by the macroelectrode.

Of particular advantage is the measure whereby the macrotherapy electrode, in the guide tube can be moved to a predetermined position and at least sections thereof can be uncovered in this position. Such pre-determined position obtained with the aid of the probe unit can be retained very simply and reliably with the guide tube. Moreover, the macroelectrode position in the guide tube can be fixed at the head skin of a patient during an operation without the risk of losing the already adjusted position even though the electrode is subsequently exposed.

For exposing the macroelectrode, the length of the guide tube is variable. Preferably, a telescopic guide tube is used for this purpose and the guide tube can be locked at any extension lengths.

The microfiber electrode may also be integrated in the probe unit so that it can be fixed with the probe unit at the manipulator. Preferably, the probe unit has a microelectrode carrier unit for the pick-up and guiding of the microfiber electrode as well as a microelectrode manipulator for the controlled movement of the microfiber electrode. In this way, an especially accurate and reliable movement of the electrode is obtained. In addition to the electronic processing of the position data, the microelectrode manipulator includes an mechanical-optical position detector for the recording and display of the microelectrode position. As the electronic position detector enables the simultaneous sensing and recording of the position data of the microelectrode with the aid of a PC-supported data acquisition unit and the display of the exact micrometer position of the data gained on a PC-monitor, the mechanical-optical indication of the position permits the direct indication of the travel distance of the microelectrode with an accuracy of 1 mm. Therefore, it serves as a countercheck for the neurosurgeon for the indirect electronic position indication of the microelectrode. Altogether, the documentation of the operation is substantially simplified and is much more precise. Furthermore, the gained data are excellently suitable for a postoperative scientific evaluation.

It is advantageous if the microelectrode carrier unit has a guide tube that can accept a microfiber electrode and can be introduced into the guide tube of the carrier unit when the probe unit is attached to the manipulator. As a result, if a certain position of the probe unit and also the guide tube has been established by an earlier measurement with the microfiber electrode, the guide tube assumes the position required for the introduction of the stimulation electrode without any further adjustment.

In a particular embodiment, the microfiber electrode includes conductors embedded in quartz glass, especially one central conductor surrounded by three symmetrical outer conductors in a slightly spaced relationship. This configuration forms a tetrode with very small dimensions so that the probability of recording in a small space is considerably improved. Presently, only a single channel recording system is available worldwide which is offered by Axon Instruments, Inc. It is called Guideline 3000. It has no motor drive of the microfiber electrode.

Preferably, the outer diameters of the microfiber electrode, the central conductor and the outer conductors have a relation to each other in the area of 6:1, 5:1 to 5:1, 2:1. A high selectivity is obtained mainly with an embodiment in which the microfiber electrode has a pointed tip on which the conductors are exposed so as to form sensor areas. The central conductor forms a cone-shaped tip and the outer conductors form elliptical area. In this way, relatively large sensor areas are obtained with a small electrode diameter, whereby the probability of detecting the neurons is greatly increased.

If the conductor consists of a high strength metal, for example, of a platinum-tungsten alloy (Pt95/W5), the probe has a very high buckling resistance so that it can also be introduced without any problems into layers with high tenacity, i.e. dura.

In order to control the advance of the microelectrode, it is advantageous if the microelectrode manipulator is provided with a microprocessor which can determine the target coordinates (x, y, z respectively, R, φ) for the probe unit utilizing the position and activity data. The output signals provided by the microprocessor may also generate visible and/or audible indications, i.e. an acoustic pattern transmitted by loudspeakers, which may be helpful during the operation. In this way, a surgeon is able to identify a target area on the basis of the neuronal action impulse pattern along the microelectrode travel path.

Besides, the establishment and the use of the recorded data are relatively simple because the output signals of the micro processor are directly supplied to a data storage device. In the data storage device, the data are stored and can be retrieved whenever necessary. This facilitates and accelerates the evaluation considerably.

Further characteristics, details and advantages of the invention will become apparent from the following description of preferred embodiments of the invention on the basis of the drawings:

BRIEF DESCRIPTION OF THE DRAWINGS

FIG. 4a shows a microfiber electrode, FIG. 4b is an enlarged view of the tip of the microfiber electrode of FIG. 4a, and FIG. 5 is an enlarged cross-sectional view of the microfiber electrode of FIG. 4a.

DESCRIPTION OF PREFERRED EMBODIMENTS

Figure 1:
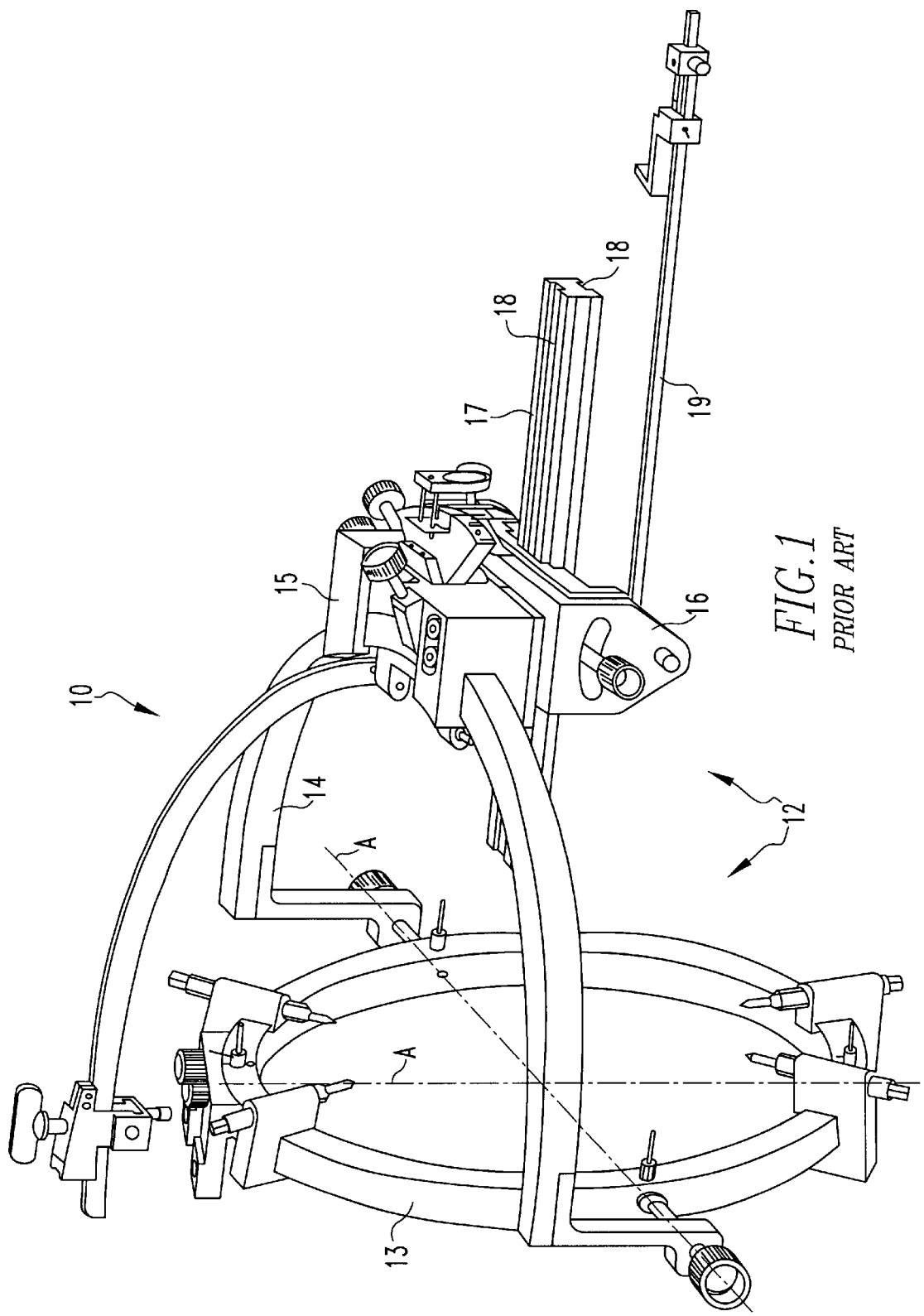
FIG. 1 is a schematic representation of a target location arrangement for a microprobe system.
Figure 2:
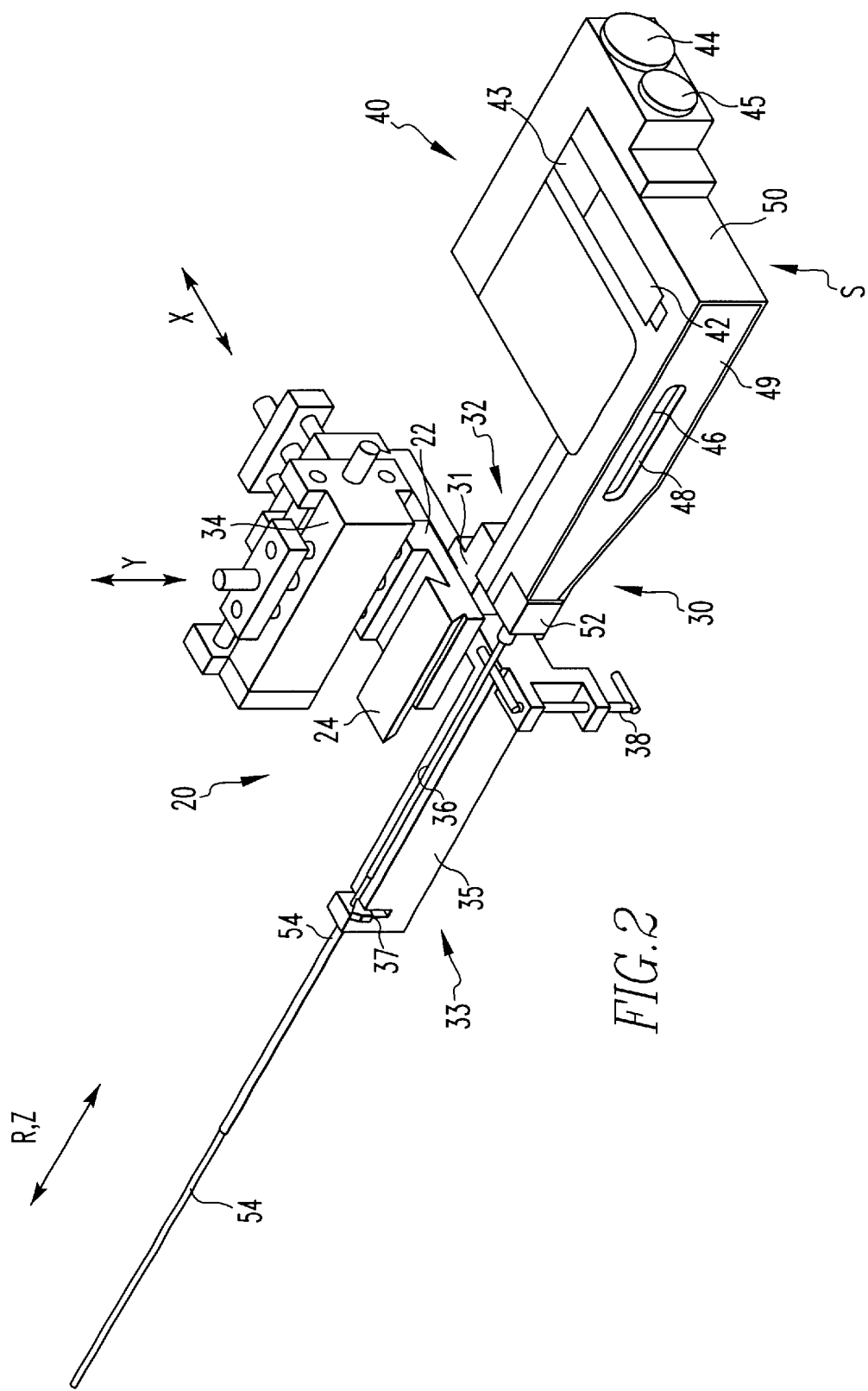
FIG. 2 is a perspective view of a manipulator with an adapter.

The microprobe system shown in FIGS. 1 and 2 consists essentially of a target locating arrangement 10 (FIG. 1) to be fixed on the head of a patient (not shown) as well as a manipulator 30 (FIG. 2) to be fixed on the target locating arrangement 10 with an adapter 20. This manipulator serves as a support unit for a probe unit S with a microelectrode manipulator 40, which moves a microelectrode 60 (not visible in FIGS. 1 and 2) guided in a microelectrode carrier unit 50. Furthermore, the manipulator 30 serves as positioning unit for a (also not shown) macro therapy electrode (brain pacemaker electrode) after removal of the probe unit S.

FIG. 1 shows the target location arrangement 10 in the form of a stereotaxic apparatus 12, for example of the type Riechert-Mundinger, RM (company Howmedica Leibinger, Freiburg, BRD). In this system, the target points and trepanation points are shown represented by Cartesian coordinates. Each point in the brain or at the basal skull of the patient can be calculated in advance and exactly targeted from each point situated outside. The apparatus 12 consists of a base ring 13 and a slewing bow 14. The head of the patient can be fixed immovable in the base ring 13, whereby the stereotactic coordinate system is established. At the outer vertex of the slewing bow 14, which is substantially semicircular, a probe unit mounting structure 15 is attached which is provided with a mounting portion 16 connected to a sensor guide rail 17. This sensor guide rail has dovetail grooves 18 formed in its upper and lower sides. A depth sensing needle 19 is also part of the apparatus 12, which is fixed to the mounting portion 16 (capable of a horizontal sweep) with the slewing bow 14 over about an axis A.

The adapter 20 has a base body 22 with a dovetail member 24 for the fixation of the manipulators 30 at the target location arrangement 10. This dovetail device is tightly fitted into the lower dovetail groove 18 of the guide rail 17 and is inserted until it engages a stopping point which is defined by the depth sensing needle 19 of the stereotoxic apparatus 12. This point is defined for example by the base body 22 of the adapter 20 or by another component connected to the adapter that engages the sensing needle 19. The engagement point provides for an always reproducible final position at which the adapter 20 will be stopped. The position is adjustable by a locking screw (not shown) so that a rigid connection between the manipulator 30 and the stereotoxic apparatus 10, 12 with respect to the Cartesian coordinate system will be achieved. The manipulator 30 follows exactly each movement of the slewing bow 14 around the slewing axis A.

In order to permit mounting of the xyz-manipulator also to other types of stereotaxic systems, the adapter 20 can be adjustable. It is for example possible to choose a type of mounting structure other than the dovetail arrangement. It is important that the manipulator 30 is connected, without freedom of movement, to the slewing bow 14 of the stereotaxic apparatus 12 and that it can be positioned in an always reproducible manner.

For the fixing of the probe unit S on the manipulator 30 preferably another dovetail connection 32 is provided between the manipulator 30 and the microelectrode manipulator 40. This connection includes a (not visible) dovetail guide structure formed in the base body 31 of the manipulator 20, for example, in the shape of a groove which receives a (also not visible) dovetail retaining device formed on a housing 41 of the microelectrode manipulator 40. In order to provide also in this case for a precise and always reproducible fastening arrangement, the holding device is installed in the groove of the base body 31 in a snugly fitting relationship and is fastened in a position as defined by a stop point by means of a locking device (not shown). Instead of the dovetail connection 32, another suitable connection may be used.

As shown in FIG. 2, the xyz-manipulator 30 includes a precision adjusting device for an adjustment in three spatial directions x, y, z. With this device, the base body 31 and the probe unit S coupled thereto together with the microelectrode manipulator 40 and the microelectrode carrier unit 50 is adjustable with respect to the base body 22 of the adapter 20 and consequently with respect to the mounting portion 18 of the stereotaxic apparatus 12 for a certain distance in any spatial direction (R, φ). The removable connections 18, 24 and 32 between the mounting portion 16 and the manipulator 30, and, respectively, between the manipulator 30 and the probe unit S ensure a permanent firm relationship with the system of coordinates of the stereotaxic apparatus 12. If the macroelectrode is fixed at the manipulator 30, it can be moved along a selectable preferred direction R (for example, the z-direction).

The housing 41 of the microelectrode manipulator 40 encloses a 4-channel pre-amplifier unit with an integrated diplexer providing a stabilized power supply, as well as a (schematically shown) DC micro-motor 42 with integrated position sensor 43 and encoder. In addition, there are two multi-pole connecting plugs 44, 45 provided at the outside of the housing 41. They are used for the connection of the microelectrode manipulator 40 with a signal processing unit (via the plug 44) and a PC motor control (via the plug 45).

Figure 3:
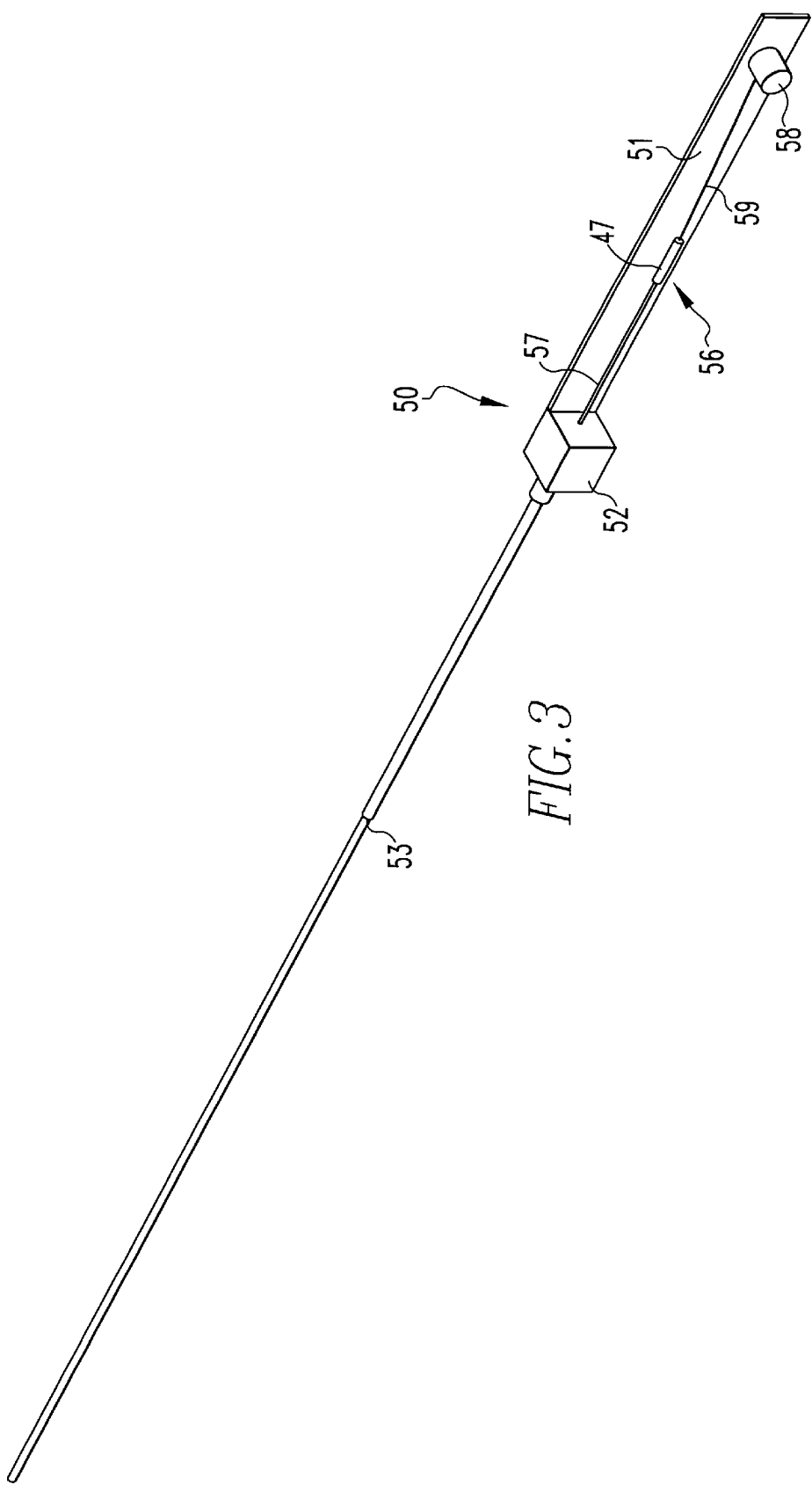
FIG. 3 is a perspective view of a microelectrode carrier unit.

The microelectrode carrier unit 50 of the probe unit S shown separately in FIG. 3 is fitted at one side into the housing 41 of the microelectrode manipulator 40 and is easily exchangeable if this should be necessary for example for the purpose of sterilization. It has a carrier plate 51 with a mounting block 52 which is disposed at the end and supports a guide tube 53 at the front side.

The guide tube 53 receives a microelectrode 60 (see FIG. 4a). A four-core quartz-platinum tungsten microelectrode (tetrode) is preferably used. This tetrode has a central conductor 64 as well as three outer conductors 66, which are arranged in a uniformly spaced relationship on a circle around the central conductor 64. For the shielding of the conductors 64, 66, a tubular metal sleeve 61 is provided. This metal sleeve is filled with quartz glass 62 in order to isolate the conductors 64, 66. The free end 63 of the microelectrode 60 has a conical tip as shown in FIG. 4b so that the central conductor 64 forms a tapered tip 65 whereas the outer conductors 67 have elliptical surface areas 67 in the conical surface area of the electrode tip 63. The tapered tip 65 and the elliptical areas 67 serve as sensors for the recording of neuronal activity signals.

The microelectrode 60 is linearly moveable in the guide tube 53 with smallest micro-increments by means of a rubber tube drive 56. The rubber tube drive 56A includes a rubber tube 57 in which the microelectrode 60 is received. At its end, the microelectrode is connected to a monofilament 59 that can be wound on and off a motor driven drum 58. (This propulsion system is described in detail in U.S. Pat. No. 5,413,103). After plugging the microelectrode unit 50 into the microelectrode manipulator 40, the drum 58 is automatically coupled and is operable by the PC-controlled micromotor 42 so that the microelectrode 60 can be moved, PC-controlled, backwards and forwards in the guide tube 53. A plastic tube (not shown) disposed in the guide tube 53 of metal will reduce the parasitic shunt-capacity between the guide tube 53 and the inner conductors 64, 66 of the tetrode 60. Due to this measure, the "howlback-effect" (principle of the capacitor microphone) caused by the shunt-capacity will be correspondingly reduced.

As shown in FIG. 2, the microelectrode carrier unit 50 disposed in the housing 41 of the microelectrode manipulator 40 is situated behind a window 48. Through this window, the movements of the rubber tube drive 56 as well as the movement and, respectively, the penetration depth of the microelectrode 60 can be monitored and determined visually. For this purpose, there may be markings on the connection 47 between the rubber tube 57 and the monofilament 59, which is movable with respect to a scale 48 provided in the window 46. With the help of this mechanical-optical position detector, even smallest relative motions of the microelectrode 60 can be easily detected and compared with calculated position values if required. Preferably, the window 46 is formed in a side wall 49 of the housing 41. This facilitates the exchange of the carrier unit 50.

For the precise support and guiding of the guide tube 53 of the microelectrode unit 50 as well as for a microtherapy electrode which can be inserted later, a carrier unit 33 is firmly mounted at the side of the base body 31 of the manipulator 30. This carrier unit has a longitudinal beam 35 with a guide groove 36 disposed at its upper edge. A telescopic guide tube which can be extended two or three times its base length is supported in the groove. The length is variable and can be set with a locking device 37 for a given extension length. The length of the main portion 54' of the telescopic guide tube 54 disposed in the groove 36 is so selected as to permit retraction of the telescopic guide tube 54 for approximately 60% of this length. This retraction length is so adjusted that the macrotherapy electrode guided therein is exposed after the retraction of the telescopic guide tube 54 for a distance of at least 10 mm above of the head skin of the patient. As a result, it is possible for the first time to position the macrotherapy electrode during surgery. This prevents a displacement of the macroelectrode when the telescopic guide tube 54 is pulled out of the head of the patient. Previously necessary position corrections which took up a great deal of time are no longer required with the use of the especially fitted telescopic guide tube 54.

During mounting of the microelectrode manipulator 40 on the xyz-manipulator 30, the guide tube 53 is inserted (after removal of a previously inserted and not shown mandrel) into the completely extended telescopic guide tube 54, which is locked in this position. Subsequently, the dovetail holding device of the microelectrode manipulator 40 is placed into the dovetail guide of the base body 31 until the (not shown) stop point is reached. In this position, the telescopic guide tube sections are locked by means of locking screws. The guide tube 53 and the telescopic guide tube 54 which covers the guide tube are accurately supported on the carrier unit 33. Both are adjusted very meticulously in z-direction of the precision adjusting device 34 of the xyz-manipulator 30 so that the microelectrode 60 will always be moved exactly in z-direction of the system of coordinates of the stereotaxic systems 10, 12.

Instead of the microelectrode 60 of the microelectrode manipulator 40, the macrotherapy electrode can be fastened to the xyz-manipulator 30. This will be done by a suitable (not shown) holder that is disposed on the manipulator 30 and inserted, during mounting, together with the guide tube 53 into the completely extended and locked telescopic guide tube 54. This way, a new macroelectrode will be adjusted so as to be positioned to extend exactly in the same direction as a previously used microelectrode 60, namely in z-direction of the manipulator 30. If the macroelectrode has reached the desired position, it can be attached to the carrier unit 33 by means of a resiliently supported locking lever 38. The lever 38 is mounted at the side of the longitudinal beam 35 of the carrier unit 33 and has a horizontal arm providing the longitudinal axis of the lever. If the locking device 37 of the telescopic guide tube 54 is unlocked and pushed back, the exactly positioned macroelectrode inserted into the patient will be accessible.

The purpose of this neuronavigation system which consists of a target location arrangement 10, an adapter 20, an xyz-manipulator 30, a probe unit S, a main amplifier filter unit with PC-supported data acquisition system, a PC-operated motor control unit and a battery power supply is to improve the radiological-anatomical target point positioning permitting improved additional electrophysiological neuronavigation.

With its carrier unit 33 and the telescopic guide tube 54 mounted on this unit, the xyz-manipulator 30 facilitates the exact positioning and adjustment of the equipment, which can be used in connection herewith. The equipment consists of the microelectrode manipulator 40, a micro cannula manipulator, a macro stimulation electrode, a macro therapy electrode or a macro coagulation electrode movable in all of the three-space axis (x-, y-, and z direction) relative to the system of coordinates of the stereotaxic apparatus 12. Each electrode is oriented exactly in z-direction of the stereotaxic apparatus 12. It is surprisingly simple to continuously adjust several parallel travel paths using the precision adjusting device 34 of the xyz-manipulator 30. An action range of ±5 mm is provided, but this range can be extended if required.

The target point is determined using the xyz-manipulator 30 and the probe unit S. After the xyz-manipulator 30 and the microelectrode manipulator 40 are coupled to the stereotaxic system 12 and adjustment of the spatial coordinates determined by a conventional anatomical-radiological target point determination with the stereotaxic system 12, the system is placed onto the head of a patient. Before this step, a stimulation is performed with the ZP-simulator in order to verify the determined data. The completely extended telescopic guide tube 54 is now ready with a mandrel disposed therein and is moved as close as possible to the suspected target location. Then the mandrel is removed and the microfiber electrode 60 is inserted. From this starting point, the brain tissue is now scanned during a slow forward motion of the 4-core quartz-platinum/tungsten microelectrode 60 using the motor driven microelectrode manipulator 40. Along the travel path, the discharge patterns of the brain nerves are sensed by the conductors 64, 66 of the microelectrode 60 and then amplified by the 4-channel preamplifier and supplied to an external (not shown) main amplifier filter unit for further signal processing. The continuous data recording is made with a PC-supported digital data acquisition system that is connected to the microelectrode manipulator 40 via the connecting plug 44. Simultaneously with the physiological signals, the position of the microelectrode is also registered. The position data are permanently recorded in the data acquisition system in parallel with the physiological data.

The position of the microelectrode 60 is recorded and indicated in duplicate. One time with the integrated DC-micromotor 42, which has an integrated position sensor 43 with encoder. Herewith the position of the microelectrode is electronically measured with $\mu$m accuracy and supplied to the PC and continuously recorded in the data storage device of the processor. The electrode position is also visually indicated on the scale 48 in the window 46 of the cover 49 of the microelectrode manipulator 40. This is a direct travel length determination (odometry) whereas the electronic odometry is an indirect method.

With the help of the characteristic discharge pattern for the individual brain cores passed by the microelectrode 60, the surgeon is able to relate the position data of the microelectrode 60 to the topographically determined brain cores. After a successful functional target point positioning, the microelectrode manipulator 40 is removed from the xyz-manipulator 30.

Subsequently, for performing the brain pacer therapy, the macrotherapy electrode is inserted into the telescopic guide tube 54, is connected to the manipulator 30 and is moved to the target point coordinates which were predetermined by the microelectrode manipulator 40 with the help of the z-propulsion of the precision adjusting device 34. After successful test stimulation, the macrotherapy electrode is connected to the carrier 33 using the macroelectrode locking lever 38 and, in this way, also in relation to the manipulator 30. Then the lock 37 of the telescopic guide tube is unlocked and the telescopic guide tube 54 is pulled back over the whole retraction distance up to the stopping point. The macrotherapy electrode which was previously inserted into the pushed back telescopic guide tube 54 is now visible through the tube above the head skin of the patient. Since the macrotherapy electrode is now accessible, the surgeon is able to fix the electrode at the head skin of the patient. Because the macrotherapy electrode is now fixed in position, a displacement is no longer possible.

Alternatively, the microelectrode manipulator 40 can be used for the positioning of a micro-cannula in the brain with $\mu$m-accuracy. Through this micro-cannula a neuro-active substance or similar substance effective for the treatment of brain diseases can be injected with the help of a micro-pump integrated into the housing 41 of the microelectrode manipulator 40.

The invention is not limited to the described embodiments, which may be varied in many different ways.

Essential advantages of all the embodiments are that the microprobe system 10, 20, 30, 40, 50 enables the neurosurgeon to be able to access the macrotherapy electrode (brain pacemaker electrode) after it is accurately positioned at the target point without the risk of losing the earlier accurate set point. Rather the surgeon can, prior to the removal of the stereotaxic apparatus 12, locate the electrode at the head skin of the patient in such a way that the electrode will remain at the desired position when the apparatus 12 is removed. Furthermore, the positioning of an applicator for the interstitial implantation of radioactive isotopes in the form of seeds is possible. Also, conceivable is an additional functional target point determination of a brain tumor providing for a classic radiological representation. To this end, radioactive seeds can be placed at a coordinate location determined with the help of an applicator that is adapted to the microprobe system according to the invention.

It is apparent that the xyz-manipulator 30 fulfills essentially the following tasks:

Support for the microelectrode manipulator 40 or (alternatively depending on the application) a microcannula manipulator and their coupling at the stereotaxic system 10.

Support for the macroelectrode for performing a macrostimulation or a tissue coagulation (for example, in case of Pallidotomie or Thalamotomie) and coupling of the macroelectrode at the stereotaxic system 10.

Support for the implantable macrotherapy electrode and its coupling at the stereotaxic system 10.

Positioning of the macrotherapy electrode at the target point coordinates which were determined with the microelectrode manipulator 40 for the purpose of a macrostimulation or a tissue coagulation.

Positioning of the implantable macrotherapy electrode at the target point coordinate determined with the microelectrode manipulator 40.

Mechanical securing of the macroelectrode, that is the implantable macrotherapy electrode in a position for an optimal therapy effect due to the use of the macroelectrode locking lever 38, the telescopic guide tube 54 and the locking of the telescopic guide tube 37, Variable adjustment of the x-, y-, and z-position of the telescopic guide tube 54 in the area of ±5 mm (xy direction) and in the area of 0 to 20 mm (z-direction) around a zero position with the aid of the precision adjusting device 34.

Furthermore, the xyz-manipulator is used as follows:

adjustment of the depth stop needle 19 of the stereotaxic system 12 relatively to the xyz-manipulator 30, insertion of the telescopic guide tube 54 with a mandrel up to the predefined stop point (z-propulsion=0) with the help of a depth stop 19, locking of the telescopic guide tube 54 with the locking device 37 and removal of the mandrel, adjustment of the precision of the adjusting device 34 in z-direction to the zero point and respectively, the starting point, adjustment of the position −10 with z-propulsion, leaving the depth stop 19 in place, insertion of the microelectrode manipulator 40 with the guide tube 53 into the telescopic guide tube 54 until the position determined by the depth stop 19 is reached, then attachment at this point, Driving the microelectrode 60 forward with the PC-motor control until the maximum penetration depth is reached. Permanent determination of the position with online analysis of the measured signals (starting point +20 mm), Return of the electrode and removal of the microelectrode manipulator 40 with the microelectrode 60, Placing a (not shown) stop ring of the macroelectrode on the connection 32 and inserting the macroelectrode into the telescopic guide tube 54. Wedging the macroelectrode with locking lever 38. The tip of the macroelectrode is now disposed in the iso-center, Determining an ideal position of the electrode with electrostimulation and modification of the z-propulsion of the precision adjusting device 34, disconnecting the telescopic guide tube 54 and pulling it back up to the rear stop, Fixing the macroelectrode at the head skin of the patient, Removing the mandrel from the macroelectrode, Removing the xyz-manipulator 30. The telescopic guide tube 54 is pulled over the macroelectrode, Finally, shifting the electrode.

The microelectrode manipulator 40 has the following properties and functions:

μm-accurate positioning of a microelectrode 60 (single- or multi-electrode) in the brain for the recording of nerve signals or for the performing of a microstimulation, μm-accurate positioning of a microcannula (single-, or multi-microcannula) in the brain for the injection of neuroactive substances, manipulated cells or similar, permanent registration of the microelectrode/microcannula position with the electronic position sensor 43 coupled with the micro-motor 43, parallel registration of the microelectrode/microcannula position with an optical position sensor by means of a window and a millimeter scale in the cover 49 of the microelectrode manipulator 18, positioning of the microelectrode 60/microcannula with different, continuously adjustable speeds and a travel direction to be chosen, Motion-error reduced positioning of the microelectrode 60/microcannula with the rubber tube drive 56, Avoidance of a hysteresis effect during the positioning of the microelectrode/microcannula with the rubber tube device 56, Improvement of the signal/disturbance difference by an integrated shielding concept of the microelectrode manipulator 40. The shielding is already present just off the microelectrode tip. There are no connecting wires extending unprotected through the air! The microelectrode manipulator with its metal housing 41 provides for a uniform shielding of the cables for signal transmission and the power supply. Furthermore, the guide tube 53 and the telescopic guide tube 54 consist of metal.

Reduction of the "microphonic effect" due to reduction of the shunt capacity of the guide tube 53 of the microelectrode support unit 50. The shunt capacity was decreased by the use of a plastic tube 55 inserted into the metal guide tube 54 of the microelectrode carrier unit.

The microprobe system according to the invention for use in medicine, namely in neurophysiology and neurosurgery, has a target determination arrangement 10 which can be fixed to the head of a patient with an adjustable mounting device 16. An adapter 20 is connectable to this mounting device in an accurately fitting manner. The adapter carries a manipulator 30 with a removable probe unit S that can be moved in a controlled manner using an arrangement 34 that is electrically controllable according to spatial coordinates (x, y, z or, respectively, R, φ). The probe unit S has a guide tube 53 for an exchangeable micro-fiber electrode 60, for example, a tetrode, which is equipped with sensor areas 65, 67 on a pointed tip for the recording of brain activity signals. They can be stored with a PC-interface in a data acquisition unit and evaluated immediately or later with an—for example—acoustical and/or optical output unit. The adapter 20 or, respectively, the manipulator 30 has a control unit, for example, a cross-slide or an XYZ-slide 34 with setscrews and scales as well as a base body 31 for the attachment of the mounting device 16 in a predetermined orientation for example by fitting a rail 24 into a guide groove 18. The macroelectrode is lockable to a support unit 33 of the manipulator 30, for example, by a locking lever 38 or a clamp or a similar device. An eccentric bar is provided for the locking of the telescopic guide tube 54 of the probe unit S to a longitudinal beam 35 of the carrier unit 33 of the manipulator 30.

What is claimed is:

1. A microprobe system for stereotactic neurotherapy, comprising:
   a target-determining arrangement for mounting on a patients head, including an adjustable support device, an adapter removably attached to said support device, a manipulator supported by said adapter, a drive unit which is electrically controllable for moving said manipulator based on spatial coordinates (x, y, z—respectively, R, φ) relative to the target determining arrangement, and a manipulator including a probe unit, an exchangeable microfiber electrode mounted on said probe unit in a predetermined orientation and including sensor areas for the sensing of neuronal activity signals, said microfiber electrode being contained in an extendable and retractable telescopic guide tube of variable length and being movable in a controlled manner together with said probe unit in a predetermined direction, said probe unit including an electronic position sensor providing electrode position data displayed simultaneously with neuronal activity signals generated by said microfiber when moving through brain tissue, and means for storing said position data and said neuronal activity signals.

2. A microprobe system according to claim 1, wherein said microfiber electrode is replaceable by a macro therapy electrode, which can be mounted on said probe unit in place of said microfiber electrode for performing specific electrical stimulations, while said manipulator carries the macrotherapy electrode is moved in a controlled manner along said predetermined direction on the basis of the stored position data provided by said microfiber electrode.

3. A microprobe system according to claim 2, wherein said manipulator includes a carrier unit providing for the alignment and guiding of the guide tube and the microfiber electrode and/or the macrotherapy electrode along said predetermined direction.

4. A microprobe system according to claim 3, wherein said microelectrode and said macrotherapy electrode can be alternately inserted in said guide tube.

5. A microprobe system according to claim 4, wherein said macro therapy electrode, when inserted in said guide tube, is lockable in a position wherein said electrode can be at least partially exposed.

6. A microprobe system according to claim 1, wherein said extendable, telescopic tube can be locked at any extension length.

7. A microprobe system according to claim 1, wherein said microfiber electrode is integrated into said probe unit and this unit is mounted, together with said electrode, on said manipulator.

8. A microprobe system according to claim 6, wherein said probe unit includes a microelectrode support unit for the guiding and position recording of the microelectrode and said microfiber electrode support unit includes a microfiber electrode manipulator for the controlled moving of said microfiber electrode.

9. A microprobe system according to claim 8, wherein said microfiber electrode manipulator includes a mechanical-optical position detector for the registration and display of the microelectrode position.

10. A microprobe system according to claim 9, wherein said microfiber electrode support unit includes a fiber guide tube receiving said microfiber electrode and adapted to be inserted into said telescopic guide tube of said support unit.

11. A microprobe system according to claim 10, wherein said microfiber electrode includes conductors embedded in quartz glass, comprising one central conductor and three outer conductors which surround said central conductor symmetrically in radially spaced relationship.

12. A microprobe system according to claim 11, wherein outer diameters of the microfiber electrode and the outer diameters of said central conductor and said outer conductors have a ratio to one another in the area of 6:1, 5:1 to 5:1, 2:1, respectively.

13. A microprobe system according to claim 12, wherein said microfiber electrode has a pointed tip where said conductors are exposed so as to form sensor areas, said central conductor forming a tapered tip and said outer conductors forming elliptical areas.

14. A microprobe system according to claim 11, wherein said conductors consist of high-tensile strength metal.

15. A microprobe system according to claim 14, wherein said conductors consist of a platinum-tungsten alloy (Pt95/W5).

16. A microprobe system according to claim 1, wherein said microelectrode manipulator is connected to a microprocessor capable of determining the target coordinates (x, y, z, respectively R, φ) of said manipulator on the basis of position and activity data recorded in said data storing means.

17. A microprobe system according to claim 16, wherein at least one of a visual and an audible signal is provided by said microprocessor to indicate certain positions of, or values, sensed by said microfiber electrode.

18. A system according to claim 17, wherein initial signals provided by said microprocessor are directly supplied to a data storage unit, in which they are recorded and from which they can be retrieved.

* * * * *